United States Patent
Vanholsbeeck (10) Patent No.: US 10,788,424 B2
(45) Date of Patent: Sep. 29, 2020

(54) OPTICAL DETECTION OF FLUORESCENCE

(71) Applicant: AUCKLAND UNISERVICES LIMITED, Auckland (NZ)

(72) Inventor: Frederique Vanholsbeeck, Auckland (NZ)

(73) Assignee: Auckland Uniservices Limited, Auckland (NZ)

(*) Notice: Subject to any disclaimer, the term of this patent is extended or adjusted under 35 U.S.C. 154(b) by 90 days.

(21) Appl. No.: 15/550,483

(22) PCT Filed: Feb. 12, 2016

(86) PCT No.: PCT/NZ2016/050014
§ 371 (c)(1),
(2) Date: Aug. 11, 2017

(87) PCT Pub. No.: WO2016/130025
PCT Pub. Date: Aug. 18, 2016

(65) Prior Publication Data
US 2018/0024065 A1   Jan. 25, 2018

(30) Foreign Application Priority Data
Feb. 13, 2015 (NZ) ........................... 705001

(51) Int. Cl.
*G01N 21/64* (2006.01)
*A61B 5/00* (2006.01)
*A61B 5/1459* (2006.01)

(52) U.S. Cl.
CPC ....... *G01N 21/6428* (2013.01); *A61B 5/0071* (2013.01); *A61B 5/7203* (2013.01);
(Continued)

(58) Field of Classification Search
CPC ............ G01N 21/6428; G01N 21/6486; A61B 5/0071; A61B 5/7203
(Continued)

(56) References Cited

U.S. PATENT DOCUMENTS

| | | | | |
|---|---|---|---|---|
| 6,132,958 A | * | 10/2000 | Simon | G01N 33/52 435/4 |
| 2007/0037135 A1 | * | 2/2007 | Barnes | G01N 21/31 435/4 |

(Continued)

OTHER PUBLICATIONS

International Search Report issued in PCT/NZ2016/050014; dated Jun. 16, 2016.
(Continued)

*Primary Examiner* — David P Porta
*Assistant Examiner* — Abra S Fein
(74) *Attorney, Agent, or Firm* — Studebaker & Brackett PC (57) ABSTRACT

A system for quantifying fluorescence elicited on a substance or sample. The system has an excitation light source configured to direct light to an waveguide network. The network has a probe tip adapted to transmit excitation light to the sample and receive fluorescence light elicited from the sample. A detector is configured to receive fluorescence light from the waveguide network and output a signal corresponding to the fluorescence light power, and a control system including a memory component configured to store signal to noise ratio threshold values.

14 Claims, 5 Drawing Sheets

(52) U.S. Cl.
CPC ........ *G01N 21/6486* (2013.01); *A61B 5/1459* (2013.01); *A61B 5/7246* (2013.01); *A61B 5/7264* (2013.01); *A61B 2562/0233* (2013.01); *G01N 21/6408* (2013.01)

(58) Field of Classification Search
USPC ..................................................... 250/459.1
See application file for complete search history.

(56) References Cited

U.S. PATENT DOCUMENTS

| | | | |
|---|---|---|---|
| 2007/0154938 A1* | 7/2007 | Oshida | G01N 21/6428 435/6.11 |
| 2008/0214457 A1* | 9/2008 | Deschenes | C07K 14/705 514/1.1 |
| 2010/0213063 A1* | 8/2010 | Zenhausern | G01N 21/645 204/452 |
| 2011/0041582 A1* | 2/2011 | Kim | B21C 23/002 72/253.1 |
| 2011/0109962 A1* | 5/2011 | Cui | G01N 21/6456 359/385 |
| 2012/0300205 A1 | 11/2012 | Misener et al. | |
| 2013/0307952 A1 | 11/2013 | Ishihara | |
| 2014/0275843 A1* | 9/2014 | Piccirillo | A61B 5/14556 600/301 |

OTHER PUBLICATIONS

Lakowicz; Principles of Fluorescence Spectroscopy; Third Edition; Springer; 2006; pp. 27-60.

* cited by examiner

OPTICAL DETECTION OF FLUORESCENCE

FIELD OF THE INVENTION

The invention generally relates to the detection and enumeration of microorganisms, and in particular to a method, system and device for improving the accuracy of fluorescence signal quantification.

BACKGROUND

Quantification of microorganisms is an essential microbiological task for many industrial, commercial and research applications. For example, detection of bacterial organisms is important for food safety, extending the shelf life of retail products and mitigating consumer risk. In another example, detecting a change in cell characteristics is important for monitoring biological processes.

Methods for detecting and quantifying microorganisms include what is known as viable bacterial plate count. The plate count technique is based on determining the number of colony forming units grown from a sample placed on agar. The number of colonies grown is dependent on the number of single cells in the original liquid and is representative of the number of viable cells.

However, the plate count method is disadvantaged by limited accuracy. Only cells able to grow and form colonies under the conditions of the test, such as incubation time, temperature, agar content and oxygen conditions, can be counted. Further, a colony does not necessarily represent a single cell and most often represents only cells that have enough physical separation on the plate to be distinguishable.

A further disadvantage of the plate count method is that colony growth requires incubation times which can vary between one and eight days depending on the type of microorganism, the agar and incubation condition. Industrial and commercial applications of plate count technology would greatly benefit from a faster measurement time.

Spectroscopy is a faster method for detecting and quantifying microorganisms as an alternative to the plate count method. Spectroscopy relies upon a phenomenon where a microorganism fluoresces when stimulated by an excitation light source. The intensity of fluorescent light emitted is indicative of the concentration of the microorganism. Devices for eliciting fluorescence from microorganisms on a sample typically utilise an excitation light source arranged to emit light to be absorbed by a sample and a detector arranged to receive fluorescent light emitted by the sample in response. However, there is a disadvantage associated with known spectroscopic detection methods where microorganisms under analysis are partially or wholly destroyed by the excitation light source, limiting or preventing any elicited fluorescence response and leading to inaccurate measurements.

It is an object of the present invention to provide detection method, system or device for detecting bacteria that goes some way toward ameliorating the abovementioned disadvantages, or that at least provides the public with a useful choice.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

SUMMARY OF THE INVENTION

In one broad aspect the invention consists in a method of quantifying fluorescence elicited from a substance or sample comprising recording an optical background noise power measurement, and the steps of:
  transmitting excitation light to the substance or sample for a first period of time,
  recording one or more optical fluorescence power measurements during the transmission of the excitation light,
  determining a signal to noise ratio (SNR) from one or more of the recorded power measurements and the optical fluorescence power,
  comparing the SNR to a threshold, and
  determining a fluorescence quantification measure from the one or more optical fluorescence power measurements when the SNR meets or exceeds the threshold.

In some embodiments, the method further comprises the step of determining the SNR is below the threshold, then, the steps of:
  transmitting excitation light to the sample for a further period of time that is longer than the previous period of time,
  recording an optical fluorescence power measurement during the transmission of the excitation light,
  determining a SNR from the recorded power measurement,
  comparing the SNR to the threshold,
  determining a fluorescence quantification measure from the one or more optical fluorescence power measurements when the SNR is above the threshold.

In some embodiments, the power measurement comprises integrating the output of an optical detector arranged to receive optical fluorescence power from the substance or sample during transmission of excitation light.

In some embodiments, the optical background noise power is integrated over an time period matching the period of time in which excitation light is transmitted to the sample and a the time period where the SNR has been determined to be meet or exceed the SNR threshold.

In some embodiments, determining the fluorescence quantification measure further comprises subtracting the background noise power measurement from the one or more optical fluorescence power measurements.

In some embodiments, the SNR threshold is a SNR of: 25, 20, 15, 10 or 5.

In some embodiments, SNR threshold is a SNR corresponding to an excitation light transmission time determined to avoid photobleaching of the substance or sample.

In some embodiments, the first time period is determined by the steps of:
  transmitting excitation light to the sample, and, for each of a plurality of time intervals, recording one or more an optical fluorescence power measurements during the transmission of the excitation light,
  determining fluorescence quantification information corresponding to each discrete time interval, and
  identifying the time interval corresponding to the onset of photobleaching, wherein the first time period is defined by a time less than or equal to that time interval corresponding to the onset of photobleaching.

In some embodiments, the onset of photobleaching is identified from one or more of:
  a knee in the fluorescence quantification information corresponding to the discrete time intervals, and/or
  fluorescence quantification information having a first rate of change transitioning to fluorescence quantification information having a second rate of change, and/or
  fluorescence quantification information having a first rate of change transitioning to fluorescence quantification information having a nonlinear rate of change.

In some embodiments, the method further comprises determining a microorganism quantification measure from the fluorescence quantification information.

In some embodiments, the step of transmitting excitation light and the step of recording an optical fluorescence power measurement are synchronised so as to expose the sample to excitation light only when the optical fluorescence power measurement is made.

In some embodiments, the step of transmitting excitation light is controlled by an optical shutter configured to have two states comprising a state where excitation light is allowed to pass and a state where excitation light is blocked.

In some embodiments, the method further comprises measuring the power of the excitation light transmitted to the sample,
  determining whether any fluctuations in excitation light power occurred, and
  adjusting the optical fluorescence power measurement to compensate for any fluctuation in excitation light power.

In another broad aspect the invention consist in a device for quantifying fluorescence elicited from a substance or sample comprising:
  a control system comprising a processor and a memory component configured to store signal to noise ratio threshold values corresponding to the substance or sample, wherein the processor is programmed to:
    record an optical background noise power measurement,
    output a signal operable to transmit excitation light to the substance or sample for a first period of time,
    record one or more optical fluorescence power measurements during the transmission of the excitation light,
    determine a SNR from one or more of the recorded power measurements and the optical fluorescence power,
    compare the SNR to a threshold stored in the memory component, and
    determine a fluorescence quantification measure from the one or more optical fluorescence power measurements when the SNR meets or exceeds the threshold.

In some embodiments, the processor is programmed to determine the SNR is below the threshold, then:
  output a signal operable to transmit excitation light to the sample for a further period of time that is longer than the previous period of time,
  record an optical fluorescence power measurement during the transmission of the excitation light,
  determine a SNR from the recorded power measurement,
  compare the SNR to the threshold,
  determine a fluorescence quantification measure from the one or more optical fluorescence power measurements when the SNR is above the threshold.

In some embodiments, the power measurement comprises integrating the output of an optical detector arranged to receive optical fluorescence power from the substance or sample during transmission of excitation light.

In some embodiments, the processor is programmed to integrate the optical background noise power over an time period matching the period of time in which excitation light is transmitted to the sample and a the time period where the SNR has been determined to be meet or exceed the SNR threshold.

In some embodiments, the processor is programmed to determine a fluorescence quantification measure further by subtracting the background noise power measurement from the one or more optical fluorescence power measurements.

In some embodiments, the SNR threshold is a SNR of: 25, 20, 15, 10 or 5.

In some embodiments, SNR threshold is a SNR corresponding to an excitation light transmission time determined to avoid photobleaching of the substance or sample.

In some embodiments, the processor is programmed to determine the first time period by the steps of:
  outputting a signal operable to cause the transmission of excitation light to the sample, and, for each of a plurality of time intervals, record one or more an optical fluorescence power measurements during the transmission of the excitation light,
  determining fluorescence quantification information corresponding to each discrete time interval, and
  identifying the time interval corresponding to the onset of photobleaching, wherein the first time period is determined by a time less than or equal to that time interval corresponding to the onset of photobleaching.

In some embodiments, the onset of photobleaching is identified from one or more of:
  a knee in the fluorescence quantification information corresponding to the discrete time intervals, and/or
  fluorescence quantification information having a first rate of change transitioning to fluorescence quantification information having a second rate of change, and/or
  fluorescence quantification information having a first rate of change transitioning to fluorescence quantification information having a nonlinear rate of change.

In some embodiments, the processor is further programmed to determine a microorganism quantification measure from the fluorescence quantification information.

In some embodiments, the processor is programmed to synchronise transmission excitation light and recording an optical fluorescence power measurement so as to expose the sample to excitation light only when the optical fluorescence power measurement is made.

In some embodiments, the processor is programmed to output a signal operable to control an optical shutter configured to have two states comprising a state where excitation light is allowed to pass and a state where excitation light is blocked.

In some embodiments, the processor is further programmed to measure the power of the excitation light during transmission to the sample,
  determine whether any fluctuations in excitation light power occurred, and
  adjust the optical fluorescence power measurement to compensate for any fluctuation in excitation light power.

In another broad aspect the invention consist in a system configured for quantifying fluorescence elicited on a substance or sample comprising:
  an excitation light source configured to direct light to an waveguide network, wherein the network comprises a probe tip adapted to transmit excitation light to the substance or sample and receive fluorescence light elicited from the substance sample, a detector configured to receive fluorescence light from the waveguide network and output a signal corresponding to the fluorescence light power, and a control system comprising a processor and a memory component configured to store signal to noise ratio threshold values corresponding to the substance or sample, wherein the processor is programmed to:

store, in the memory component, an optical background noise power measurement, output a signal operable to transmit excitation light to the substance or sample for a first period of time, store, in the memory component, one or more optical fluorescence power measurements during the transmission of the excitation light, determine a SNR from one or more of the recorded power measurements and the optical fluorescence power, compare the SNR to a threshold stored in the memory component, and determine a fluorescence quantification measure from the one or more optical fluorescence power measurements when the SNR meets or exceeds the threshold.

In some embodiments, the processor is programmed to determine the SNR is below the threshold, then:

output a signal to the excitation light source to initiate transmission of excitation light to the sample for a further period of time that is longer than the previous period of time, receive, from the optical detector, one or more measurements of the optical fluorescence power during the transmission of the excitation light, determine a SNR from the received power measurement, compare the SNR to the threshold, determine a fluorescence quantification measure from the one or more optical fluorescence power measurements when the SNR is above the threshold.

In some embodiments, the power measurement comprises integrating the output of the optical detector arranged to receive optical fluorescence power from the substance or sample during transmission of excitation light.

In some embodiments, the processor is programmed to integrate the optical background noise power over an time period matching the period of time in which excitation light is transmitted to the sample and a the time period where the SNR has been determined to be meet or exceed the SNR threshold.

In some embodiments, the processor is programmed to determine a fluorescence quantification measure further by subtracting the background noise power measurement from the one or more optical fluorescence power measurements.

In some embodiments, the SNR threshold is a SNR of: 25, 20, 15, 10 or 5.

In some embodiments, SNR threshold is a SNR corresponding to an excitation light transmission time determined to avoid photobleaching of the substance or sample.

In some embodiments, the processor is programmed to determine the first time period by the steps of:

outputting a signal operable to cause the transmission of excitation light to the sample, and, for each of a plurality of time intervals, record one or more an optical fluorescence power measurements during the transmission of the excitation light, determining fluorescence quantification information corresponding to each discrete time interval, and identifying the time interval corresponding to the onset of photobleaching, wherein the first time period is determined by a time less than or equal to that time interval corresponding to the onset of photobleaching.

In some embodiments, the onset of photobleaching is identified from one or more of:

a knee in the fluorescence quantification information corresponding to the discrete time intervals, and/or fluorescence quantification information having a first rate of change transitioning to fluorescence quantification information having a second rate of change, and/or fluorescence quantification information having a first rate of change transitioning to fluorescence quantification information having a nonlinear rate of change.

In some embodiments, the processor is further programmed to determine a microorganism quantification measure from the fluorescence quantification information.

In some embodiments, the processor is programmed to synchronise transmission excitation light and recording an optical fluorescence power measurement so as to expose the sample to excitation light only when the optical fluorescence power measurement is made.

In some embodiments, the excitation light source further comprises an optical shutter configured to have two states comprising a state where excitation light is allowed to pass and a state where excitation light is blocked, wherein processor is programmed to output a signal operable to control the state of the optical shutter.

In some embodiments, the processor is further programmed to measure the power of the excitation light during transmission to the sample, determine whether any fluctuations in excitation light power occurred, and adjust the optical fluorescence power measurement to compensate for any fluctuation in excitation light power.

In another broad aspect the invention consists in a method for quantifying fluorescence elicited from a substance or sample comprising recording an optical background noise power measurement, and the steps of:

transmitting excitation light to the substance or sample, measuring optical fluorescence power emitted from the substance or sample during the transmission of the excitation light, determining a signal to noise ratio (SNR) from one or more of the recorded power measurements and the optical fluorescence power at one or more intervals during the transmission of the excitation light, stopping the transmission of excitation light to the substance or sample when the SNR is determined to meet or exceed a SNR threshold, and determining a fluorescence quantification measure from the measured optical fluorescence power measurement.

In some embodiments, the power measurement comprises integrating the output of an optical detector arranged to receive optical fluorescence power from the substance or sample during transmission of excitation light.

In some embodiments, the optical background noise power is integrated over an time period matching the period of time in which excitation light is transmitted to the sample and a the time period where the SNR has been determined to be meet or exceed the SNR threshold.

In some embodiments, determining the fluorescence quantification measure further comprises subtracting the background noise power measurement from the one or more optical fluorescence power measurements.

In some embodiments, the SNR threshold is a SNR of: 25, 20, 15, 10 or 5.

In some embodiments, SNR threshold is a SNR corresponding to an excitation light transmission time determined to avoid photobleaching of the substance or sample.

In some embodiments, the SNR threshold is determined by the steps of:
- transmitting excitation light to the sample, and, for each of a plurality of time intervals, recording one or more an optical fluorescence power measurements during the transmission of the excitation light,
- determining fluorescence quantification information corresponding to each discrete time interval, and
- identifying the SNR corresponding to the onset of photobleaching, wherein the SNR threshold is defined by a SNR less than or equal to that time interval corresponding to the onset of photobleaching.

In some embodiments, the onset of photobleaching is identified from one or more of:
- a knee in the fluorescence quantification information corresponding to the discrete time intervals, and/or
- fluorescence quantification information having a first rate of change transitioning to fluorescence quantification information having a second rate of change, and/or
- fluorescence quantification information having a first rate of change transitioning to fluorescence quantification information having a nonlinear rate of change.

In some embodiments, the method further comprises determining a microorganism quantification measure from the fluorescence quantification information.

In some embodiments, the step of transmitting excitation light and the step of recording an optical fluorescence power measurement are synchronised so as to expose the sample to excitation light only when the optical fluorescence power measurement is made.

In some embodiments, the step of transmitting excitation light is controlled by an optical shutter configured to have two states comprising a state where excitation light is allowed to pass and a state where excitation light is blocked.

In some embodiments, the method further comprises measuring the power of the excitation light transmitted to the sample,
- determining whether any fluctuations in excitation light power occurred, and
- adjusting the optical fluorescence power measurement to compensate for any fluctuation in excitation light power.

In another broad aspect the invention consists in a method for quantifying fluorescence elicited on a substance or sample comprising recording an optical background noise power measurement, and the steps of:
- recording one or more optical fluorescence power measurements during transmission of the excitation light to the sample for a first period of time, wherein the first period of time is determined as a time period in which the optical fluorescence power drops from an initial fluorescence power to a first fraction of the initial fluorescence power, and
- determining a fluorescence quantification measure from the one or more optical fluorescence power measurements.

In some embodiments, the method further comprises determining a SNR from one or more of the recorded optical fluorescence power measurements and the background noise power measurement,
- comparing the SNR to a threshold,
- determining a fluorescence quantification measure when the SNR meets or exceeds the threshold.

In some embodiments, the method further comprises determining the signal to noise ratio to be below the threshold, then the steps of:
- recording one or more optical fluorescence power measurements during transmission of the excitation light to the sample for a first period of time, wherein the first period of time is determined as a time period in which the optical fluorescence power drops from an initial fluorescence power to a fraction lower than the first fraction of the initial fluorescence power, and
- determining a fluorescence quantification measure from the one or more optical fluorescence power measurements.

In some embodiments, the first fraction is between 5 and 15%, or, the first fraction is 10%.

In some embodiments, the method further comprises determining a microorganism quantification measure from the fluorescence quantification measure.

In another broad aspect the invention consist in a device for quantifying fluorescence elicited from a substance or sample comprising:
- a control system comprising a processor and a memory component configured to store signal to noise ratio threshold values corresponding to the substance or sample, wherein the processor is programmed to:
- record one or more optical fluorescence power measurements during transmission of the excitation light to the sample for a first period of time, wherein the first period of time is determined as a time period in which the optical fluorescence power drops from an initial fluorescence power to a fraction lower than the first fraction of the initial fluorescence power, and
- determine a fluorescence quantification measure from the one or more optical fluorescence power measurements.

In another broad aspect the invention consist in a system configured for quantifying fluorescence elicited on a substance or sample comprising:
- an excitation light source configured to direct light to an waveguide network, wherein the network comprises a probe tip adapted to transmit excitation light to the substance or sample and receive fluorescence light elicited from the substance sample,
- a detector configured to receive fluorescence light from the waveguide network and output a signal corresponding to the fluorescence light power, and
- a control system comprising a processor and a memory component configured to store signal to noise ratio threshold values corresponding to the substance or sample, wherein the processor is programmed to:
- record one or more optical fluorescence power measurements during transmission of the excitation light to the sample for a first period of time, wherein the first period of time is determined as a time period in which the optical fluorescence power drops from an initial fluorescence power to a fraction lower than the first fraction of the initial fluorescence power, and
- determine a fluorescence quantification measure from the one or more optical fluorescence power measurements.

The following embodiments may relate to any of the above aspects. Other aspects of the invention may become apparent from the following description which is given by way of example only and with reference to the accompanying drawings.

As used herein the term "and/or" means "and" or "or", or both.

As used herein "(s)" following a noun means the plural and/or singular forms of the noun.

The term "comprising" as used in this specification means "consisting at least in part of". When interpreting statements in this specification which include that term, the features, prefaced by that term in each statement or claim, all need to be present but other features can also be present. Related terms such as "comprise" and "comprised" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

Preferred embodiments of the invention will now be described by way of example only and with reference to the accompanying drawings, in which.

DETAILED DESCRIPTION

Embodiments of the invention relate to devices, systems and methods for the quantification of fluorescence activity of microorganisms that fluoresce in response to excitation light, while avoiding or mitigating the destruction of microorganisms exposed to the excitation light. Some embodiments incorporate a versatile, time-resolved fibre probe for conducting spectroscopy measurements, herein referred to as an optrode.

The optrode is configured to allow measurement of light emitted by fluorescent reporter proteins that respond to excitation light emitted naturally or from a florescent tag molecules that bind to the microorganisms under test. Florescent tag molecules may be usefully employed to allow measurements of microorganisms that emit low or no fluorescent light naturally when stimulated.

Described herein are methods of quantification of fluorescence light for further use in determination of microorganisms, including bacteria concentration and activity monitoring, and action potential recording to cell activation and detection. For example, the quantification of florescence light elicited from organisms that have been tagged with a fluorophore or to quantify a process that is linked with a fluorophore such as action potential using a voltage sensitive dye. In this specification, references to florescence light elicited from a sample under test may be florescence light naturally emitted from the sample or emitted from tag molecules that have been added to the sample.

An optrode for measuring fluorescence requires several components to provide measurement functionality. In particular, the components comprise one or more optical fibres for coupling excitation light from a light source to a substance, and fluorescence light from the substance to a detector. One way to conduct a measurement using the optrode is to take a swab from a sample to be tested and placed in a vessel containing a solution such as saline, microorganisms on the swab are then mobilised in the solution. The tip of the optrode is then inserted into the solution. The optrode may require a particular coating and/or a particular geometry in the tip of an optical fibre to optimise transmission of light into the solution and enhance reception of fluorescence light radiated from the solution. Excitation light is transmitted to the tip via an optical network and fluoresce light is received by the tip and guided through the same and/or an auxiliary optical network to measurement devices.

Another use of an optrode is for real time deep in-vivo non-invasive measurements. For example, where an optrode probe is made up of tiny optical fibres, light can be directed to any part of the tissue under study simply by direct insertion of the fibre. Another use of the optrode is to look at different cells marked with different florescent dyes simultaneously with good specificity.

Figure 1:
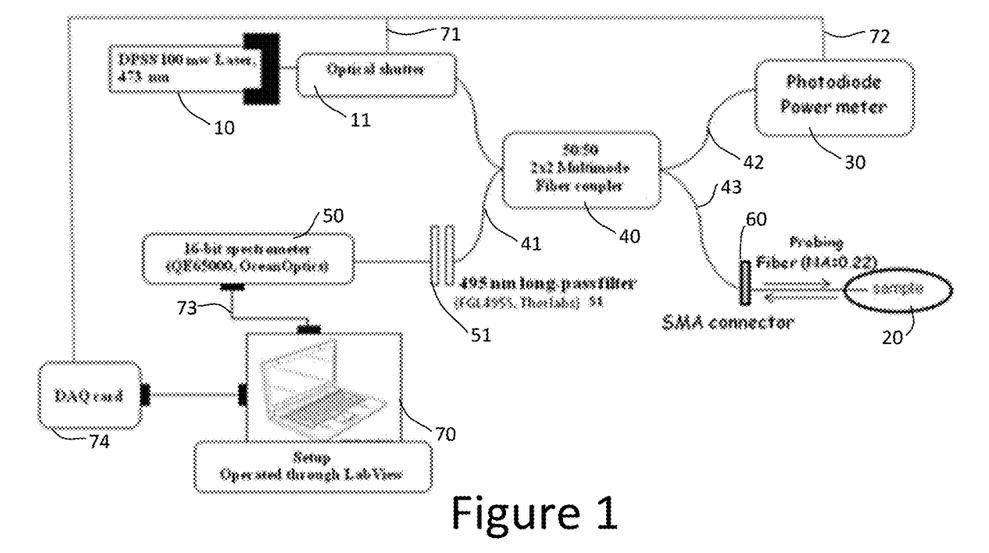
FIG. 1 shows a diagram of measurement components according to an embodiment.

FIG. 1 shows a schematic diagram of optical system components for use with an optrode and operable to make measurements to quantify fluorescence light. A light source 10 is configured to provide excitation light to a sample 20 via an optical system comprising waveguides to thereby elicit a fluorescence signal indicative of microorganism concentration in or on the sample. In some embodiments, the light source is a laser configured to output light with characteristics known to stimulate fluorescence in microorganisms or associated tag molecules in a particular sample to be tested. In other embodiments, a LED based light source is used.

In some embodiments, the light source is switched on and off quickly to provide a burst of stimulation light. In other embodiments, an optical shutter 11 is provided between the light source output and the optical waveguide to control the transmission of light into the system. An optical shutter is often desirable so that the light source can be maintained at constant stable operating conditions where they are typically most stable. A laser, for example, will often exhibit an inconsistent operating wavelength and/or power during start up and shut down phases. It is therefore advantageous to allow a laser to operate continuously and control the output transmission to the optrode system with a shutter. In some embodiments, the output of two or more light sources, each having one or more different operating wavelengths, are combined to provide a multiple wavelength light source. Two or more light sources are able to be combined using devices such as beam splitters and optical fibre couplers.

The output of the light source or optical shutter is provided to a network of optical fibres arranged to couple excitation light from light source to the sample 20 and, in some embodiments, a power meter 30. The power meter 30 is useful for checking the optical power of the light source remains consistent during a measurement procedure or at least allow input light power fluctuations to be accounted for. In some embodiments, the recorded power level of the light source is used to refine estimation of the fluorescence signal power. The power meter 30 is configured to convert received light into an electrical signal, such as a voltage having a level indicative of the power of light received, for further processing. The fibre network is further configured to couple fluorescence light from the sample to a power measurement device 50 for further analysis. A first section of optical fibre 41 is arranged to couple excitation light from the light source 10 and shutter 11 to a fibre coupler 40. The fibre coupler 40 splits the excitation light into a first optical fibre path 42 that is connected to the power meter 30. The fibre coupler 40 further splits the excitation light into a second optical fibre path 43 that leads to a probe 60. The probe is configured to couple excitation light from the fibre to the sample to elicit fluorescence light and receive fluorescence light elicited from the sample 20. The most efficient shape and size of the probe tip is often dependent on the refractive index of the sample being analysed as will be apparent to those skilled in the art.

Fluorescence light coupled into the probe 60 traverses back to the fibre coupler 40 via the entry path of optical fibre 43. The output of the fibre coupler 40 is directed to a second power measurement device 50 and in some embodiments, a long pass filter 51 is configured at the entry to ensure that only the fluorescence signal is received and any residual light from the excitation light source is blocked. The second power measurement device 50 is configured to convert received light into an electrical signal for further processing by a computational device.

In some embodiments, the system comprises an optical path that extends directly from the tip of the probe 60 to the filter 51 and the second power measurement device 50, thereby bypassing the coupler 40 and probe entry path 43. This arrangement may be advantageous by avoiding a loss of a portion of the fluorescence that is light elicited from the sample by entering the splitter and being directed to path 41 that leads back to the light source 10. This embodiment may further prove advantageous when very low fluorescence signals are present by inherently reducing the fibre autofluorescence noise incident to the second power measurement device 50.

In some embodiments, the second power measurement device 50 is an optical spectrometer configured to measure the power of received fluorescence light of one or more wavebands. In other embodiments, the second power measurement device 50 is a photodiode configured to output a signal indicative of the optical power of received fluorescence light. Other optoelectronic devices for receiving light and generating an output useful for measurement will be apparent to those persons skilled in the art.

In some embodiments, where two or more wavebands are desired to be measured independently, the system of FIG. 1 may be further modified to split the optical path to the filter 51 and second power measurement device 50 into two or more optical paths that lead to other filters and power measurement devices. For example, an optical splitter can be configured to split incoming light into two or more optical paths. In each optical path is configured a filter having optical characteristics to select a desired waveband to be measured. Such configurations may be advantageous in situations where it is desired to use power measurement devices incapable of distinguishing optical power dependent on the wavelength of received light. For example, in some embodiments the filters are a band pass filters having a centre frequency operational to pass light about the centre frequency to a wideband power measurement device and cut off light having wavelengths outside of the centre frequency. It will be appreciated that in all configurations, the centre frequency and/or pass band of any filters configured to filter light before a power measurement device will have transmission properties selected in accordance with the properties of the light desired to be received and measured.

In preferred embodiments, the optical system of FIG. 1 is contained in a lightproof housing to maximise performance the sensitivity of the system by minimising ambient or background light.

In preferred embodiments a control system is configured to control transmission of light to a sample and receive power measurements. In some embodiments, the control system is implemented by a computational device or processor configured or configurable to receive one or more analogue or digital inputs, perform calculations and make control decisions, and output one or more analogue or digital outputs operable to enable control of external devices, information display devices and/or communicate data. In some embodiments, the control system is a computer comprising processor, one or more memory components and a data acquisition interface. The processor is typically configured to carry out instruction that are stored in the memory components. The instructions may be to output signals operable to read to and write from the data acquisition interface, or interface directly to devices such as the excitation light source in order to control the operation. In other embodiments, the control system is implemented by a microprocessor which functions similarly to a computer but typically has a limited number of inputs and outputs in which to receive data signals and send control signals.

In FIG. 1, the control system 70 has a plurality of outputs configured to provide output signals and a plurality of inputs configured to receive one or more signals indicative of measurement information. In some embodiments, the control system is supplemented by an internal input and output interface 74 such as a data acquisition interface.

In particular, the control system 70 has a first output 71 configured to connect to the optical shutter 11. The output 71 is configured to control the state of the optical shutter to thereby allow or block excitation source light from the light source 10 to the sample, or alternatively, modulate the light output from the light source. The control system 70 has a further input configured to receive an input 72 from the optical power meter 72. The input from the power meter is a signal indicative of the optical power output by the light source 10. The control system 70 has a further input con- figured to receive an input from the second power measurement device 50 comprising a signal indicative of the fluorescence light elicited from the sample.

In one experimental example, the system of FIG. 1 uses a 100 mW diode pumped solid state lasers at 473 and 532 nm such as a Changchun New Industries Optoelectronics Tech. Co., Ltd. device, to excite green fluorescent protein (excitable at 473 nm) and red fluorescent protein (excitable at both 473 and 532 nm). A laser mount that includes an electronically activated optical shutter is used to control timing and duration of excitation light. Optical fibre section comprise all-silica pyrocoat high OH—, multimode, non-Hermetic optical fibre with core diameter of 200 μm and cladding diameter 220 μm.

The light from the laser and passed by the optical shutter is split with a 50/50 coupler and directed to the sample to excite microorganisms within the immediate environment around the tip of the probe, known as the collection volume. Fluorescence light elicited by the excitation light within the collection volume of the probe is returned by the same fibre and measured by a spectrometer, such as a QE65000 Ocean Optics device. A long-pass filter is placed before the spectrometer to ensure that the fluorescence signal is measured solely without any residual pump signal.

A data acquisition card, for example a USB-1608FS Measurement Computing device is used to synchronize the shutter with the spectrometer. Illumination power is monitored in real time using a photodiode, for example a 10530DAL Integrated Photomatrix Ltd. device. In some embodiments, a computer acquisition program such as LABVIEW 8.2 is configured to control the hardware and present data for analysis.

In some embodiments, principal component analysis (PCA) is used to represent the fluorescence signal. PCA allows identification of specific spectral features of the microorganism fluorescence in an aquatic environment. PCA also reduces the variance of the fluorescence signal due to fibre auto fluorescence, fluorescence broadening and/or any light scattering effect in the medium.

The photostability of the fluorescent dyes is important to ensure accuracy of fluorescence power measurement. The fluorescence intensity of a dye in the single measurement decreases exponentially due to laser excitation. An appropriate excitation light source exposure time to the sample should be used to minimise the effect of photobleaching reducing the elicited fluorescence power while preserving a signal to noise ratio that is high enough to achieve an accurate measurement. For example, SYTO 9 dye has a photobleaching half-life time of 0.95 seconds, therefore an 8 ms integration time—the time the sample is exposed to the excitation light—would not unduly affect the sample fluorescence intensity due to photobleaching causing less than a 1% change in fluorescence power.

Embodiments of the above described system are operable to accurately quantify microorganisms in or on a sample. In some embodiments, measurements are able to be improved by the following improving the sensitivity of the system and also by monitoring the laser input power. In particular, sensitivity improvements are able to be attained by the efficient delivery of 10 mW of light for in situ fluorescence excitation and detection as well as the use of a sensitive fluorescence detector, a stable 100 mW excitation laser source and an appropriate collection volume of the fibre probe. Further, by monitoring the laser power, fluctuations in laser power can be accounted for during measurement of the fluorescence signal. Synchronisation of the laser shutter allows acquisition of the fluorescence signal with a high signal to noise ratio and minimal integration time.

In preferred embodiments, a control system is configured to manage operation of the optical components and process the signals received by the detectors. In some embodiments, the control system is a computer operating software and one or more hardware interfaces. In other embodiments, the control system is a microprocessor having a number of inputs and outputs and configured to interface to various devices and process incoming signals and generate output control signals.

In particular, the control system is configured to enable quantification of microorganisms on a substance or sample desired to be tested. The control system is configured to first make a recording of the background noise power measurement received at the detector 50. The background noise power should be made with the excitation light source 10 switched off or at least the shutter 11 closed. The background noise power measurement typically comprises dark noise, or the noise floor of electronics devices including the detector 50, background optical noise such as stray light that leaks into the optical system and fibre fluorescence noise. The background noise power measurement is typically subtracted from fluorescence power measurements to give a true reading of the fluorescence power. In some embodiments, background noise power measurement further comprises immersion of the optrode tip into a solution similar to the sample but not containing any microorganisms.

In preferred embodiments, power measurements are conducted by measurement devices including spectrometers, photodiodes and other devices as will be apparent to those familiar with optical measurement equipment. Some devices, such as spectrometers, have a built in functionality for measuring optical power over a time period, for example by integrating power levels across a spectral band. For other devices, such as photodiodes, a power measurement is made by regularly measuring and recording the output voltage signal. This function can be performed, for example, by an analogue to digital converter. The signal levels recorded over a time period can be integrated in order to determine an optical power measurement. For example, embodiments utilising photodiode based power measurement devices are configured to conduct a power measurement by integrating the output of the detector over a particular time period.

The control system is configured to enable the excitation light source and/or shutter so that excitation light is transmitted through the optical fibre network to the sample for a first period of time. The period of time should be such that significant photobleaching of the sample, such as less than 1%, is unable to occur. This way the optical fluorescence power elicited from the sample remains relatively constant. The period of time the sample may be exposed to excitation light is often in the order of milliseconds. However the particular time period depends on the concentration of microorganisms in the sample and the strength of the excitation light source.

Figure 4:
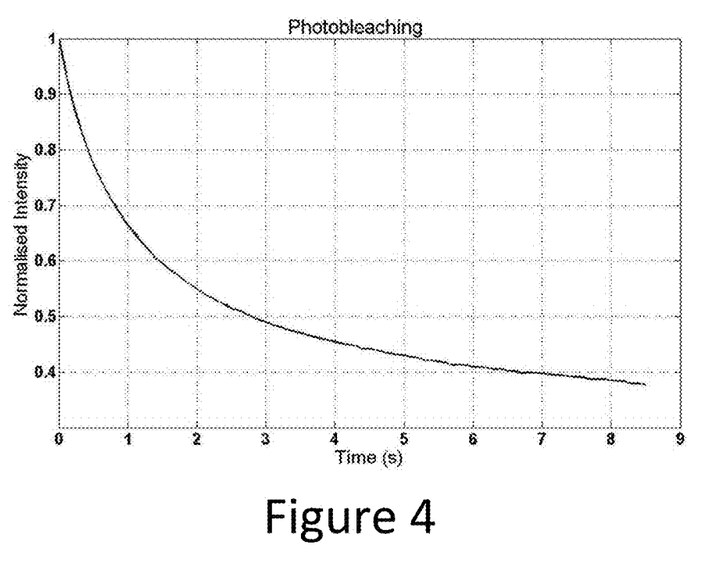
FIG. 4 shows a graph of normalised fluoresce power as a function of a lengthy exposure to excitation light.
Figure 5:
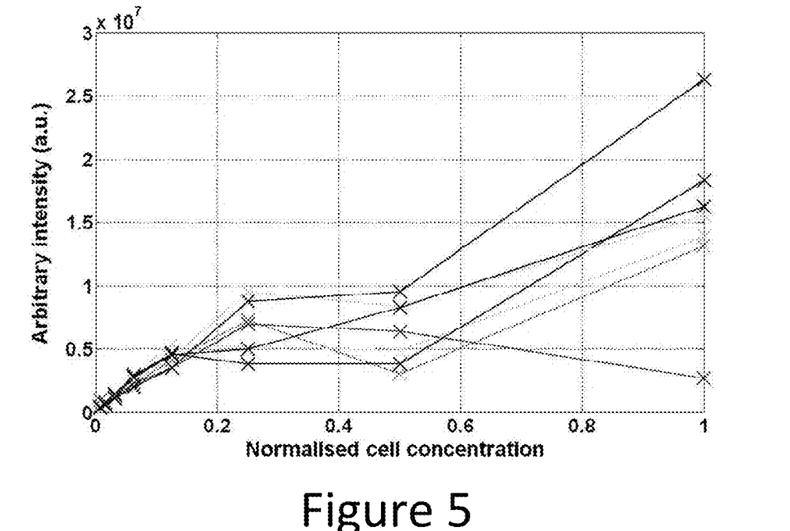
FIG. 5 shows a graph where several solutions of differing concentrations were exposed to exposure light for the same period of time.

FIG. 4 shows a graph of normalised fluoresce power as a function of a lengthy exposure to excitation light. In response to prolonged exposure, elicited fluorescence power exhibits an exponential decline, usually after a short period of stability. FIG. 5 shows a graph where several solutions of differing concentrations exposed to exposure light for the same period of time. Each of the fit lines show portions of linearity in the 0 to 0.2 region of normalised cell concentration where photobleaching is not occurring. Further, each of the fit lines in the 0.2 to 0.4 region of normalised cell concentration show a change in gradient where the onset of photobleaching occurs. The inventors have ascertained that the data presented by each fit line in the 0 to 0.2 region is characterised by a particular set of conditions where fluorescence data is measureable without suffering the onset of inaccuracies due to photobleaching. In particular, a low concentration of microorganisms is able to exhibit fluorescence for a short period before the onset of photobleaching takes place.

In preferred embodiments, the control system is configured to record the optical fluorescence power measurement elicited by the sample during the transmission of the excitation light and calculate a signal to noise ratio using the background noise power measurement and the recorded fluorescence power measurement. The signal to noise (SNR) ratio is usually indicative of the quality of the measurement made. For example, a high signal to noise ratio is usually indicative of a signal that is significantly free from being influenced by noise and thereby enables an accurate measurement. However, in present embodiments an even more accurate measurement of the optical fluorescence power elicited from a sample can be achieved using a low signal to noise ratio that ordinarily would have been thought too low a signal level to provide an accurate reading. The inventors have determined that this is because the significance of the photobleaching effect when microorganisms are exposed to excitation light contributes significantly more toward a measurement inaccuracies than measurements where the optical fluorescence power that is barely above the noise floor that also require a longer exposure time.

Figure 6:
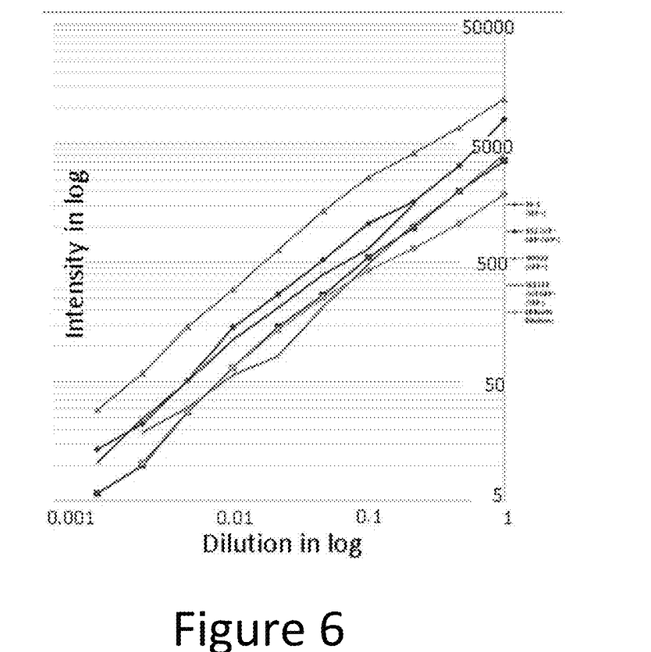
FIG. 6 shows a graph of fluorescence intensity measurements taken under conditions suitable for substantially avoiding the effects of photobleaching.

FIG. 6 shows a graph of fluorescence intensity measurements taken under conditions suitable for substantially avoiding the effects of photobleaching. The data points shown were recorded using a laser shutter that is synchronised with the recording time of the fluorescence power measuring device. Further, the integration time was kept short so as to avoid photobleaching while maintaining a low, but adequate signal to noise ratio.

To establish the elicited fluorescence power is adequately clear of the noise floor, the control system is configured to compare the calculated SNR to a threshold. In some embodiments the threshold is an SNR of at least 5, 10, 15, 20 or 25. The precise SNR threshold depends on the photostability of the microorganisms being tested. Some initial experimentation may need to be conducted to establish an ideal SNR by establishing the operational parameters that avoid photobleaching. Microorganisms with high photostability can endure measurements with a high SNR while those with a low photostability benefit from measurements with a very low SNR. Low SNR is achieved by using, for example, a low powered excitation light source and/or exposing the sample for a very short period of time.

The control system is configured to determine the SNR meets or exceeds a threshold in order for the measurements made to be accurate, and the data used to measure the microorganism quantification of the sample under test will produce an accurate result.

In one example, measurements can be taken in a sequential manner by increasing the fluorescence power acquisition time so that an appropriate SNR is able to be discovered without photobleaching in the sample. The ideal integration time is reached with the parameters corresponding to those just before the onset of photobleaching occurs. However, lower integration times and corresponding SNR may also achieve and accurate result. The procedure to make a measurement is as follows:
1. Record the background noise comprising, for example, dark noise and noise from background light sources and fibre fluorescence. The background noise can be recorded at any stage. However, for efficiency, a background noise measurement could be taken at potentially useful exposure measurement time period, for example, by starting from the shortest time and increasing by doubling the time for each measurement.
2. Make sure the laser output is at a level known to be useful for stimulating fluorescence. For example, the power should be between 5 and 10 mW.
5. Set the SNR to a target level. For example, 5, 10, 15, 20 or 25.
6. Record a measurement by using increasing exposure time periods until the desired SNR is reached or exceeded.

The procedure to analyse the results is as follows:
1. For each measurement, background noise to obtain the real fluorescence power.
2. Measure the optical fluorescence power. The obtained number is proportional to the fluorescing microorganism concentration. In some embodiments, a spectrometer is used to conduct measurements. The optical power is measured by integrating the resulting spectrum around the apparent maxima to determine the optical power in the spectrum.

Figure 2:
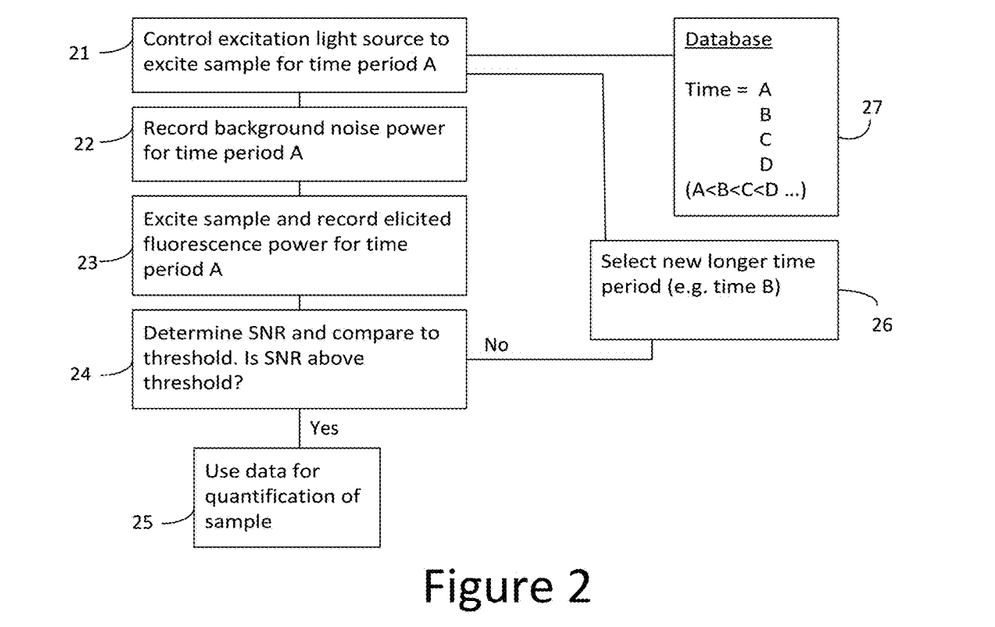
FIG. 2 shows a flow chart generally depicting a sequence of steps for conducting a measurement according to an embodiment.

FIG. 2 shows an example of a sequence of steps that may be implemented by the control system for conducting a measurement of optical fluorescence power and while minimising or avoiding the effect of photobleaching. The control system is preferably configured to conduct a sequence of optical measurements and computational functions as follows. At the first step 21, the control system is configured to determine a first exposure time, depicted as 'Time A'. In some embodiments the exposure time is provided by a database 27 configured to store a plurality of exposure times arranged in a sequence from low to high. In some embodiments, the exposure times are selected with knowledge of the optical power of the excitation light source 10 and the expected photostability of the sample 20.

At step 22 the control system is configured to conduct a background noise power measurement and stored in memory for later use. The noise power measurement should be recorded at a time that matches or substantially matches the excitation light source exposure time selected at step 21. At step 23, the control system is configured to expose the sample to the excitation light for the selected time period A and the resulting optical fluorescence power elicited from the sample is recorded during that time period. In some embodiments, the control system is configured to synchronise exposure of the excitation light to the sample and the recording of elicited fluorescence power. The response time of fluorescence elicited is in the order of microseconds and can therefore be considered instantaneous for the purpose of the measurements being made.

At step 24 the control system is configured to calculate the SNR using the background power measurement and the optical fluorescence power measurement. The control system is configured to compare the calculated SNR to a threshold. In some embodiments, the particular threshold is selected from values stored in the database 27. In other embodiments, the threshold is based on the magnitude of the signal levels received and/or the level of the calculated SNR.

At step 25 the control system is configured deem the measurement sufficiently accurate for making a calculation of fluorescence quantification if the SNR is determined to be at or above the threshold. If the SNR is below the threshold, control system is configured to proceeds to step 26 and select a longer excitation light exposure time period and the process repeated until the SNR reaches or exceeds the threshold. The fluorescence quantification information can then be used to determine information such as bacteria concentration, activity monitoring, and/or action potential recording to cell activation and detection. For example, quantification of organisms that have been tagged with a fluorophore or to quantify a process that is linked with a fluorophore such as action potential using a voltage sensitive dye.

The method expressed with reference to FIG. 2 is designed to avoid excessive exposure of the sample to excitation light. Photobleaching is at least substantially avoided by initially exposing the sample to very short bursts of excitation light and/or low intensity excitation light. The SNR threshold should be kept low in order to minimise the amount of excitation light exposed to the sample. In some embodiments, the SNR threshold is 5. However, other SNR thresholds comprising 10, 15, 20, 25, or any number in the range of, for example, 5 to 25 could be selected based on predictions, measurements or estimations of the photostability of the sample under test. In other embodiments, the SNR is initially set low, for example at 5. The method depicted in FIG. 2 is conducted and a measure of the quality of the measurement is determined from the resulting data. If the measurement is determined to be of low quality, the method can be repeated with a higher SNR threshold, for example 10.

In some embodiments, the control system is further configured to determine the stability of the output power of light source 10. FIG. 1 shows an example of a physical layout of components where the excitation light being partially split and directed to a second power meter 30 to measure the power of the excitation light source. In circumstances where the light source power is determined to be unstable or at least not substantially constant during a measurement, the resulting fluorescence power measurement could be discarded and the measurement repeated, or alternatively, the light source power fluctuation could be compensated for in the of fluorescence power measurement. Use of the optical shutter 11 allows the laser to operate continuously and therefore be more likely to have substantially stable operating characteristics.

Figure 8:
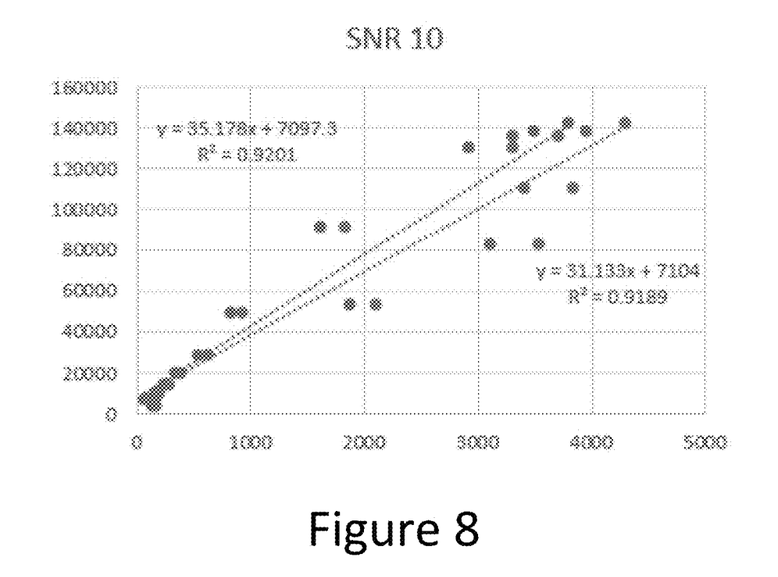
FIGS. 8 to 10 show graphs comparing fluorescence quantification data.
Figure 9:
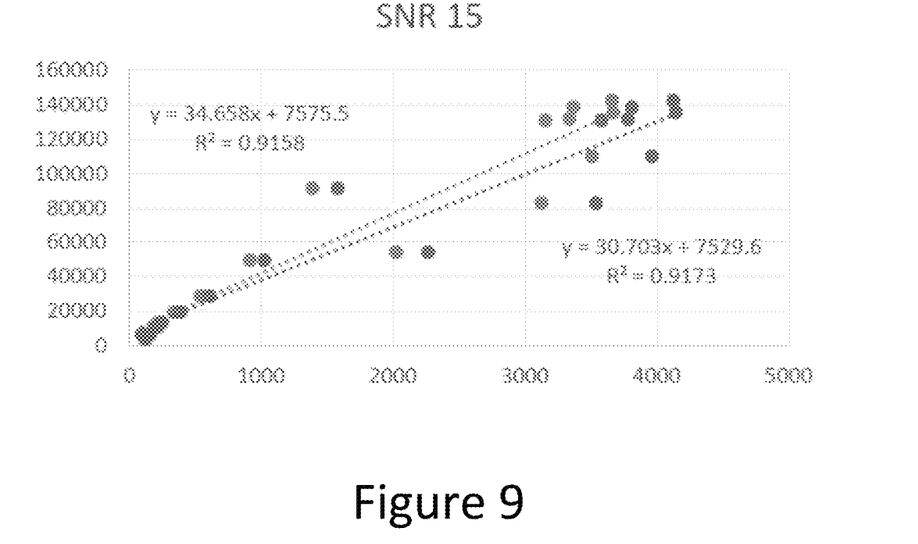
Figure 10:
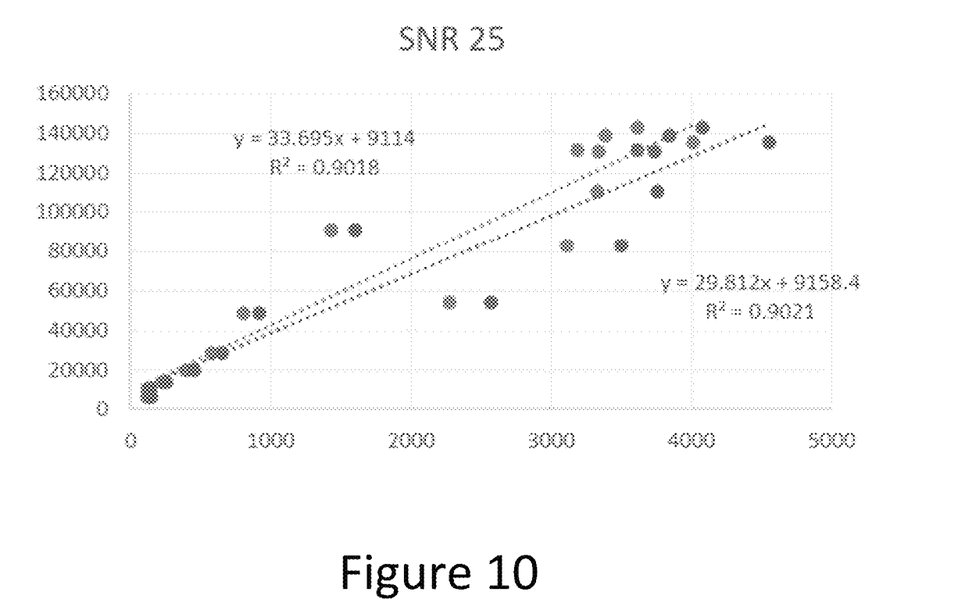

FIGS. 8, 9 and 10 show graphs of microorganism quantification data using the method generally depicted in FIG. 2 compared to measurement data obtained using the plate count method. The variable $R^2$ is indicative of the correlation between the two techniques and is in the range of 90-92% which indicates a substantial agreement between the data.

In particular, FIG. 8 shows result data where the SNR threshold has been set as low as 10. Similarly, FIGS. 9 and 10 show result data where the SNR threshold has been set to 15 and 25 respectively. Despite the low SNR, the measurement accuracy is clearly aligned with that of known yet more onerous techniques widely used in the industry. Therefore the method generally depicted by FIG. 2 offers a fast and accurate alternative to plate count measurement processes.

Figure 3:
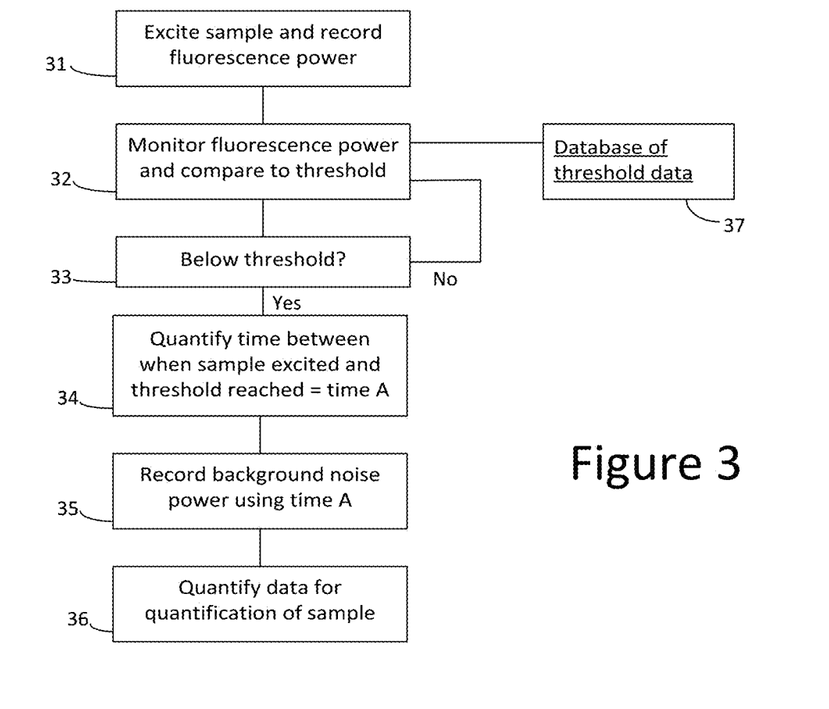
FIG. 3 shows a flow chart generally depicting a sequence of steps for conducting a measurement according to a further embodiment.

FIG. 3 shows a flow diagram of another method for quantifying microorganisms on a substance or sample. The method depicted is based on the principle of establishing a quantifiable amount of photobleaching that has occurred in the sample, and compensating for that amount to achieve proportionality with the real microorganism concentration. For example, a photobleaching effect of some known microorganisms can be modelled. Or in other words, the rate at which the fluorescence power will reduce can be predicted. It should be appreciated that the rate of reduction is dependent on factors including the intensity of the excitation light source and the concentration of microorganisms on a sample.

The control system for implementing the process of FIG. 3 is preferably configured to conduct a sequence of optical measurements and computational functions. At step 31, the control system is configured to provide excitation light to the sample to elicit a fluorescence response from any microorganisms present. The control system is configured to record a measure of the optical fluorescence power in response to the excitation light. At step 32, the controller is configured to measure the fluorescence power again after a period of time. At step 33, the controller is configured to compare the newly recorded fluorescence power to a threshold. If the fluorescence power has not dropped below the threshold, the fluorescence power is continued to be measured and compared again to the threshold, and so on until the threshold is passed.

After repeated exposure to excitation light, the sample will exhibit photobleaching and the fluorescence power relative to a constant excitation power will reduce until the fluorescence power drops below the threshold. In some embodiments, the threshold is a power level determined to be a fraction of the initially measured power level, for example, 90% of the initial power. However, in should be appreciated that the threshold could be any value that aligns with the predictability of the drop in fluorescence power due to the photobleaching effect. In some embodiments, the control system comprises a memory component configured to store threshold data. In some embodiments, the memory component is adapted to store a database 37 of threshold data for various samples and optical systems.

At step 34, the control system is configured to measure the time taken between the initial power measurement at step 31 and the time at which the fluorescence power dropped below the threshold. At step 35, the control system is configured to measure the background noise level using the time calculated at step 34 as an integration time so that a SNR may be determined.

Figure 7:
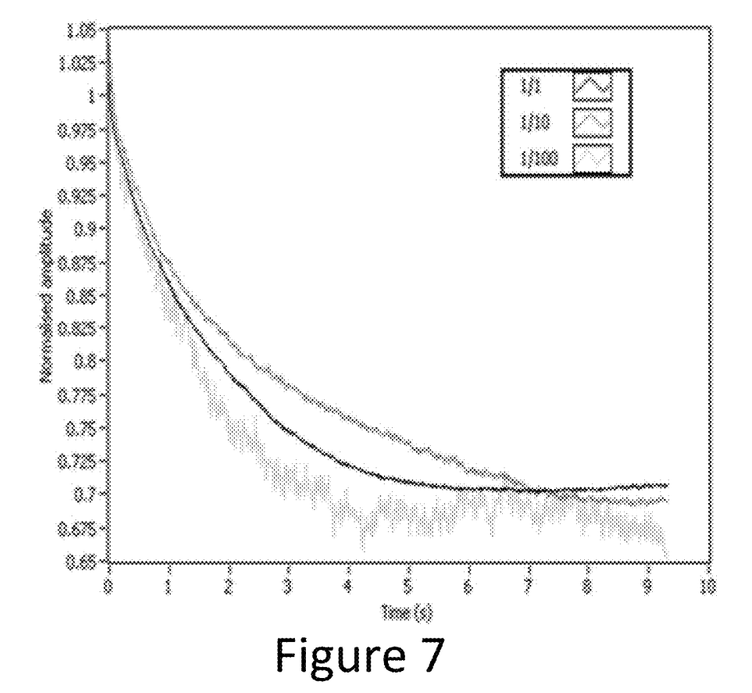
FIG. 7 shows characterisation curves of received fluorescence power able to be used to model the photobleaching behaviour.

At step 36, the control system is configured to calculate a fluorescence quantification measure of the sample using the measured fluorescence power information and background noise measurement. The fluorescence quantification information can then be used to determine information such as bacteria concentration, activity monitoring, and/or action potential recording to cell activation and detection. For example, quantification of organisms that have been tagged with a fluorophore or to quantify a process that is linked with a fluorophore such as action potential using a voltage sensitive dye. In some embodiments, a sample of the microorganisms is taken and the photobleaching curve characterised. FIG. 7 shows an example of three different characterisation curves of received fluorescence power that are able to be used to model the photobleaching behaviour of subsequent measurements, for example, by the method generally depicted in FIG. 3.

In some embodiments, the control system is configured to determine the quality of the quantification measure calculated at step 35. For example, a measure of the quality could be determined by calculation of the SNR of one or more fluorescence power measurements. In some embodiments the control system is configured to determine quantification measure to be accurate when the SNR is above a threshold. For example, the threshold could be a SNR of 5, 10, 15, 20 or 25. In some embodiments, the control system is configured to lower the fraction value at step 33 if the SNR value calculated is too low for the measurement to be determined accurate.

In further embodiments, the concentration of microorganisms is measured by determining an exposure time that corresponds to the onset of photobleaching. In these embodiments, it is considered that photobleaching will not have a significant impact on the fluorescence power for a particular period of time soon after excitation light is exposed to the sample. In other words, received fluorescence power will remain substantially constant for a short period before beginning to exhibit the effects of photobleaching. The particular time period after which the onset of photobleaching takes place is able to be determined by at least one of a knee in the concentration information corresponding to the discrete time intervals, and/or concentration information having a first rate of change transitioning to concentration information having a second rate of change, and/or concentration information having a first rate of change transitioning to concentration information having a nonlinear rate of change.

Where in the foregoing description reference has been made to elements or integers having known equivalents, then such equivalents are included as if they were individually set forth. Although the invention has been described by way of example and with reference to particular embodiments, it is to be understood that modifications and/or improvements may be made without departing from the scope of the invention as set out in the claims.

The invention claimed is:

1. A method for quantifying fluorescence elicited from a substance or sample, and substantially avoid photobleaching of the substance or sample, comprising recording an optical background noise power measurement, and the steps of:
   transmitting excitation light of a predetermined power to the substance or sample for a first period of time,
   recording one or more optical fluorescence power measurements,
   determining a fluorescence target signal to noise ratio (SNR) corresponding to an excitation light transmission time and power determined to be at or before the onset of photobleaching of the substance or sample,
   determining a fluorescence SNR from the recorded power measurements and the background noise power measurement,
   comparing the determined fluorescence SNR to the target SNR, and, when the determined fluorescence SNR meets the target SNR:
   determining a fluorescence quantification measure from the one or more optical fluorescence power measurements.

2. A method as claimed in claim 1, wherein the method further comprises the step of determining the fluorescence SNR is below the target SNR, then, the steps of:
   transmitting excitation light to the sample for a further period of time that is longer than the previous period of time and/or has greater predetermined power,
   recording an optical fluorescence power measurement during the transmission of the excitation light,
   determining a new fluorescence SNR from the recorded power measurement,
   comparing the new determined fluorescence SNR to the target SNR,
   determining a fluorescence quantification measure from the one or more optical fluorescence power measurements when the new determined fluorescence SNR meets the target SNR.

3. A method as claimed in claim 1, wherein the power measurement comprises integrating the output of an optical detector arranged to receive optical fluorescence power from the substance or sample during transmission of excitation light.

4. A method as claimed in claim 1, wherein the optical background noise power is integrated over a time period matching the period of time in which excitation light is transmitted to the sample and a time period where the fluorescence SNR has been determined to meet the target SNR.

5. A method as claimed in claim 1, wherein determining the fluorescence quantification measure further comprises subtracting the background noise power measurement from the one or more optical fluorescence power measurements.

6. A method as claimed in claim 1, wherein the target SNR is: 25, 20, 15, 10 or 5.

7. A method as claimed in claim 1, wherein the target SNR is determined by the steps of:
   transmitting excitation light to the sample, and, for each of a plurality of time intervals, recording one or more an optical fluorescence power measurements during the transmission of the excitation light,
   determining fluorescence quantification information corresponding to each discrete time interval, and
   identifying the time interval corresponding to a time less than or equal to that time interval corresponding to the onset of photobleaching, and
   determining the target SNR based on the identified time interval and power measurement.

8. A method as claimed in claim 7, wherein the onset of photobleaching is identified from one or more of:
   a knee in the fluorescence quantification information corresponding to the discrete time intervals, and/or
   fluorescence quantification information having a first rate of change transitioning to fluorescence quantification information having a second rate of change, and/or
   fluorescence quantification information having a first rate of change transitioning to fluorescence quantification information having a nonlinear rate of change.

9. A method as claimed in claim 1, wherein the method further comprises determining a microorganism quantification measure from the fluorescence quantification information.

10. A method as claimed in claim 1, wherein the step of transmitting excitation light and the step of recording an optical fluorescence power measurement are synchronised so as to expose the sample to excitation light only when the optical fluorescence power measurement is made.

11. A method as claimed in claim 1, wherein the step of transmitting excitation light is controlled by an optical shutter configured to have two states comprising a state where excitation light is allowed to pass and a state where excitation light is blocked.

12. A method as claimed in claim 1, wherein the method further comprises measuring the power of the excitation light transmitted to the sample,
   determining whether any fluctuations in excitation light power occurred, and
   adjusting the optical fluorescence power measurement to compensate for any fluctuation in excitation light power.

13. A device for quantifying fluorescence elicited from a substance or sample, and substantially avoid photobleaching of the substance or sample, comprising:
   a control system comprising a processor and a memory component configured to store signal to noise ratio threshold values corresponding to the substance or sample, the processor programmed to undertake the steps of:
   recording an optical background noise power measurement, determine a fluorescence target signal to noise ratio (SNR) corresponding to an excitation light transmission time and power determined to avoid photobleaching of the substance or sample, transmitting excitation light of a pretermined power to the substance or sample for a first period of time, recording one or more optical fluorescence power measurements during the transmission of the excitation light, determining a fluorescence SNR from one or more of the recorded power measurements and the optical fluorescence power, comparing the determined fluorescence SNR to the target SNR, and when the signal to noise ratio meets the target SNR;

determining a fluorescence quantification measure from the one or more optical fluorescence power measurements.

14. A system configured for quantifying fluorescence elicited on a substance or sample comprising:

an excitation light source configured to direct light to a ail waveguide network, wherein the network comprises a probe tip adapted to transmit excitation light to the sample and receive fluorescence light elicited from the sample, a detector is configured to receive fluorescence light from the waveguide network and output a signal corresponding to the fluorescence light power, and a control system comprising a memory component configured to store signal to noise ratio threshold values, the control system configured to perform the steps of:

recording an optical background noise power measurement, determine a target fluorescence signal to noise ratio (SNR) corresponding to an excitation light transmission time and power determined to avoid photobleaching of the substance or sample, transmitting excitation light of a predetermined power to the sample for a first period of time:

recording one or more optical fluorescence power measurements during the transmission of the excitation light, determining a fluorescence signal to noise ratio from one or more of the recorded power measurements, comparing the determined fluorescence signal to noise ratio to a target SNR stored in the memory component, and, when the signal to noise ratio meets the target SNR:

determining a fluorescence quantification measure from the one or more optical fluorescence power measurements.

* * * * *